United States Patent [19]

Price

[11] 3,952,050
[45] Apr. 20, 1976

[54] CYCLOPENT [a] INDENE COMPOUNDS

[75] Inventor: Barry John Price, London, England

[73] Assignee: Allen & Hanburys Limited, London, England

[22] Filed: Apr. 3, 1973

[21] Appl. No.: 347,477

[30] Foreign Application Priority Data
Apr. 14, 1972  United Kingdom............... 17222/72

[52] U.S. Cl. .................. 260/501.1; 260/293.62; 260/247; 260/618 F; 260/247.2 R; 260/553 R; 260/573; 260/576; 260/570.5 C; 260/570.5 P; 260/501.18; 260/566 A; 260/456 R; 260/566 R; 424/269; 424/267; 424/325; 260/590 FB
[51] Int. Cl.² ........................................ C07C 87/40
[58] Field of Search ................ 260/501.1, 576, 573, 260/501.18, 570.5 C, 570.5 P

[56] References Cited
UNITED STATES PATENTS

| | | | |
|---|---|---|---|
| 3,291,828 | 12/1966 | Kotera et al. ................. | 260/576 X |
| 3,385,885 | 5/1968 | Kitahonoki et al. ............ | 260/576 X |
| 3,704,323 | 11/1972 | Krapcho ........................ | 260/576 |

OTHER PUBLICATIONS

Muller, Houben–Weyl, Methoden der Organischen Chemie, pp. 676–677 (1955).
Clemo, Chemical Abstracts, Vol. 46, Col. 2034d–e (1952).

*Primary Examiner*—Bernard Helfin
*Assistant Examiner*—G. Breitenstein
*Attorney, Agent, or Firm*—Bacon & Thomas

[57] ABSTRACT

Indane derivatives of general formula (I):

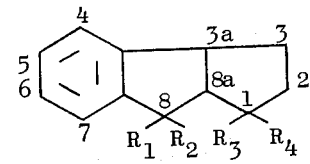

in which:
R$_1$ and R$_2$ represent a hydrogen atom, a lower alkyl group, preferably containing 1 to 6 and particularly 1 to 4 carbon atoms, or an arylalkyl group, or together form a cycloalkyl ring containing 3–6 carbon atoms; R$_3$ is a hydrogen atom or a lower alkyl preferably containing 1 to 6 and particularly 1 to 4 carbon atoms; R$_4$ represents the group —NR$_5$R$_6$ in which R$_5$ and R$_6$ may be the same or different and each represent a hydrogen atom, a carbamoyl group or a lower alkyl radical preferably containing 1 to 6 and particularly 1 to 4 carbon atoms which may optionally be substituted by amino, alkylamino, dialkylamino, hydroxy, aryl or aroyl groups which aroyl groups may be substituted; or in which R$_5$ and R$_6$ may be joined to form a ring optionally containing other hetero atoms; and non-toxic pharmaceutically acceptable salts and esters thereof. The compounds have marked analgetic activity and are devoid of respiratory depressant action.

27 Claims, No Drawings

CYCLOPENT [a] INDENE COMPOUNDS

This invention relates to novel indane derivatives having biological activity and to compositions containing the same.

The present invention provides indane derivatives of general formula (I):

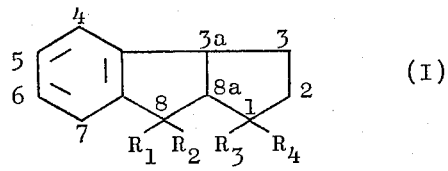

in which:
$R_1$ and $R_2$ represent a hydrogen atom, a lower alkyl group preferably containing 1 to 6 and particularly 1 to 4 carbon atoms, or an arylalkyl group, or together form a cycloalkyl ring containing 3–6 carbon atoms; $R_3$ is a hydrogen atom or a lower alkyl preferably containing 1 to 6 and particularly 1 to 4 carbon atoms; $R_4$ represents the group $-NR_5R_6$ in which $R_5$ and $R_6$ may be the same or different and each represent a hydrogen atom, a carbamoyl group or a lower alkyl radical preferably containing 1 to 6 and particularly 1 to 4 carbon atoms which may optionally be substituted by amino, alkylamino, dialkylamino, hydroxy, aryl or aroyl groups which aroyl groups may be substituted; or in which $R_5$ and $R_6$ may be joined to form a ring optionally containing other hetero atoms; and non-toxic pharmaceutically acceptable salts and esters thereof.

The compounds of general formula (I) possess asymmetric centers and the invention also includes all the possible diastereoisomers and enantiomers thereof. Particularly useful salts of the compounds according to the invention are acid addition salts, such as those with mineral acids, e.g., hydrochloric and sulphuric acid and those with organic acids, e.g., tartaric and maleic acids.

Particularly preferred meanings for the groups $R_1$ and $R_2$ are hydrogen $C_{1-4}$ alkyl, in particular methyl, or benzyl. Particularly preferred meanings for $R_3$ are hydrogen or $C_{1-4}$ alkyl in particular methyl. Particularly preferred meanings for $R_5$ and $R_6$ are hydrogen, $C_{1-4}$ alkyl substituted by $C_{1-4}$ alkylamino or by $C_{1-4}$ dialkylamino or by phenyl or by 4-fluorobenzoyl or in which the groups together with the adjacent nitrogen atom form a morpholino or piperidino moiety; another preferred group for $R_5$ or $R_6$ is carbamoyl ($-CONH_2$). Specific preferred compounds and salts are those the preparation of which is described in the Examples. The compounds of the invention have marked analgetic activity and are devoid of respiratory depressant action. Furthermore no Straub Index can be recorded nor is the analgetic action significantly antagonised by nalorphine. These characteristics are often associated with non-narcotic analgetics in man. For example, in Table I, the compound 1,2,3,3aα,8,8aα-hexahydro-N-methylcyclopent[a]inden-1α-amine, maleate (AH 9197) and the diastero-isomer 1,2,3,3aα,-8,8aα-hexahydro-N-methylcyclopent[a]inden-1β-amine maleate (AH 8538) are compared with codeine in standard pharmacological tests for evaluating analgetic action. The N-ethyl analogue of AH 9197 (N-ethyl-1,2,3,3aα,8,8aα-hexahydrocyclopent[a]inden-1α-amine) maleate (AH 9903) is also included.

TABLE I

| Test | Route | Ex. 1 9197 | Ex. 2 9903 | Ex. 3 8538 | Codeine |
|---|---|---|---|---|---|
| Phenylquinone Writhing test | $ED_{50}$p.o. | 7.4 | 4.6 | 11.9 | 5.8 |
| Hot plate | $ED_{50}$s.c. | 0.44 | 2.2 | 15.0 | 11.8 |
|  | p.o | 10 | 9.5 |  | 15.5 |
| Dog Tooth-pulp Stimulation | Minimum effective dose p.o. | 3.7 | <5.0 | 5.0 | 3.3 |

All figures are in mg/kg.
p.o. = per os
s.c. = sub cutaneous

The invention also provides pharmaceutical compositions which contain an indane derivative of general formula I or a salt thereof, with a pharmaceutically acceptable carrier.

The pharmaceutical compositions according to the invention, may be formulated for use in the conventional manner with the aid of carriers as excipients and formulatory agents as required and with or without supplementary medicinal agents.

Oral administration is most convenient in the form of tablets (which may or may not be coated), capsules or liquid preparations. Carriers, include inert diluents such as lactose, calcium sulphate or calcium phosphate and/or disintegrating agents such as starch or alginic acid. Magnesium stearate may be used as a lubricating agent. For liquid oral formulations suspending agents such as sodium carboxymethyl cellulose may be used together with preservatives and flavouring or sweetening agents such as sucrose, dextrose and glycerol.

Injections may be formulated with the aid of physiologically acceptable carriers and agents as solutions, or as dry products for reconstitution before use.

The dosage at which the active ingredient is administered may vary within a wide range. A suitable oral dosage range is generally from 5–500 mg. For intramuscular or subcutaneous injection a suitable dosage range is from 1–100 mg. The pharmaceutical compositions may, with advantage, be formulated to provide a dose within these ranges either as a single unit or a number of units.

The compounds according to the invention may be prepared from the ketone of general formula (II):

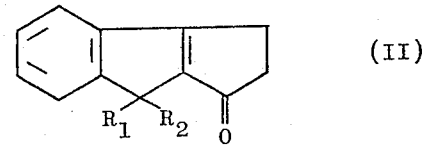

Where $R_1 = R_2 = H$ this may be alkylated by conventional procedures, for example with alkyl or arylalkyl halides and a strong base such as sodium hydride or alkoxide in the presence of a solvent to give ketones (II) where $R_1$ and $R_2$ have the meanings other than hydrogen. αω-Dihalides give rise to compounds of the invention in which $R_1$ and $R_2$ together form d cycloalkyl rings.

The unsaturated ketones (II) may be reductively aminated with an amine $R_5R_6NH$ (wherein $R_5$ and $R_6$ have the meanings already stated), for example with hydrogen in the presence of a noble metal catalyst to give compounds of general formula (I) ($R_3 = H$, $R_4 = NR_5R_6$). The reaction can be carried out in two stages if desired, the first being catalytic hydrogenation, for example with palladium charcoal, to give saturated ketones of general formula (III), where $R_1$ and $R_2$ have the meanings already stated. This is followed by reductive amination

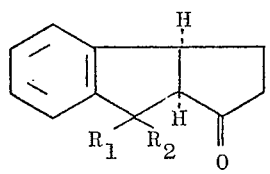
(III)

as before. Reductions of the oximes of compounds of general formulae (II) and (III) similarly give the compounds of the invention (IV; $R_5$ and $R_6 = H$).

The main products from the process of catalytic reduction usually have the stereochemical configuration shown in formula (IV),

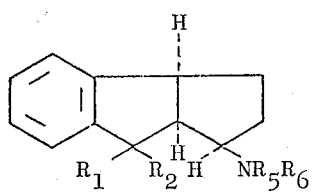
(IV)

arising from all cis addition of hydrogen from the catalyst surface.

Stereospecific synthesis of the diastereoisomer of general formula (V):

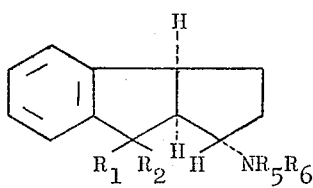
(V)

is possible by utilizing the tosylate of the general formula (VI) (X = Tosyl). Displacement of this group with amines $R_5R_6NH$ proceeds with inversion of

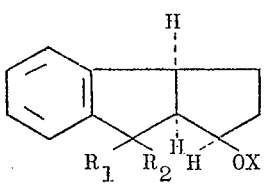
(VI)

configuration.

The necessary parent alcohol (VI) (X = H) may be obtained by reduction of compounds of formula (III) with a complex metal hydride, for example sodium borohydride.

Compounds of the invention where $R_3$ is alkyl may be obtained from the ketone (III) as shown in the flowchart.

FLOWCHART

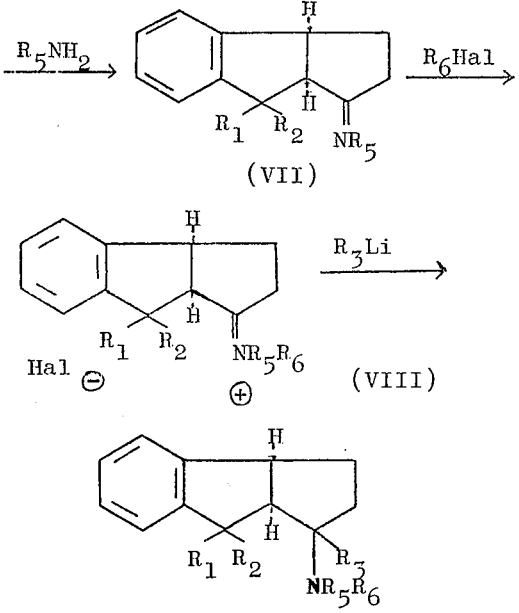

The azomethine (VII) is treated with a conventional alkylating agent ($R_6Hal$) and the quaternary salt (VIII) then reacts with an organometallic derivative, e.g., an organolithium compound $R_3Li$ to give the required compounds.

Compounds of the invention where $R_5$ and $R_6$ have one of the meanings given may be converted into compounds with other meanings by conventional chemical processes. For example where $R_5/R_6$ represents one or more hydrogen atoms, the compound may be converted by direct or reductive alkylation into structures in which $R_5/R_6$ is a lower alkyl radical optionally substituted as already defined. Similarly, reaction with an alkali metal cyanate, such as sodium or potassium cyanate, gives compounds of the invention where $R_5$ represents a carbamoyl group. Examples of these conversions are described in the Examples.

The invention therefore provides a process for the preparation of compounds of the general formula:

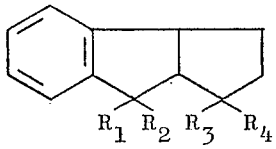

in which:
$R_1$ and $R_2$ represent a hydrogen atom, a lower alkyl group, or an arylalkyl group, or together form a cycloalkyl ring containing from 3 to 6 carbon atoms;

$R_3$ represents a hydrogen atom or a lower alkyl group;

$R_4$ represents the group $-NR_5R_6$ in which $R_5$ and $R_6$ may be the same or different, each represent a hydrogen atom, a carbamoyl group or a lower alkyl radical, which lower alkyl radical may optionally be substituted by an amino, alkylamino, dialkylamino, hydroxy, aryl or aroyl groups which aroyl groups may be further substituted; or in which $R_5$ and $R_6$ may together represent a ring which may additionally contain other hetero atoms.

which comprises:

a. reductively aminating a ketone of the formula:

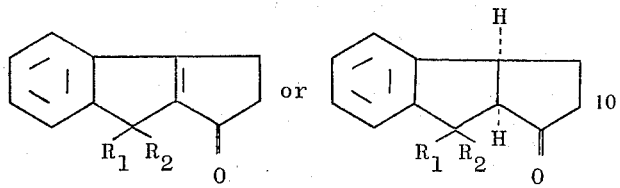

in which $R_1$ and $R_2$ have the meanings given above with an amine of the formula $R_5R_6NH$ in which $R_5$ and $R_6$ have the meanings given above, whereby compounds in which $R_3$ is hydrogen and $R_4$ is $-NR_5R_6$ are produced.

b. reducing an oxime of the formula:

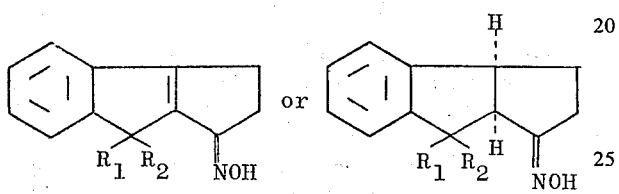

in which $R_1$ and $R_2$ have the meanings given above, to give compounds in which $R_3$ is hydrogen and $-NR_5R_6$ is $NH_2$.

c. for the production of compounds in which $R_1$ and $R_2$ have the meanings given above, $R_3$ is hydrogen and $R_4$ has the meaning $-NR_5R_6$ reaction of the corresponding tosyl ester

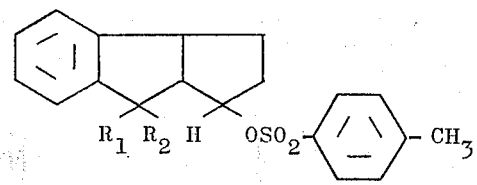

with an amine of the formula $R_5R_6NR$ in which $R_5$ and $R_6$ have the meanings given above.

d. reacting a compound of the formula:

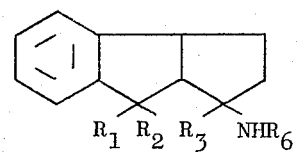

with sodium cyanate to give a compound in which $R_4$ is $-NR_5R_6$ where $R_5$ is $-CONH_2$ (carbamoyl) and $R_1$, $R_2$, $R_3$ and $R_6$ have the meanings given above.

e. reacting a compound of the formula:

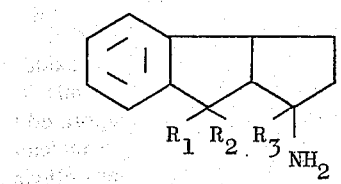

in which $R_1$, $R_2$ and $R_3$ are hydrogen with formaldehyde to give the compound in which $R_4$ is $-NR_5R_6$ in which $R_5$ and $R_6$ are both methyl.

f. for the production of compounds in which $R_3$ is alkyl reacting a compound of the formula:

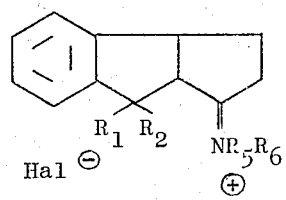

with an organolithium compound $R_3Li$ in which $R_1$, $R_2$, $R_3$, $R_5$ and $R_6$ have the meanings given above and Hal is halogen.

g. alkylating a compound of the formula:

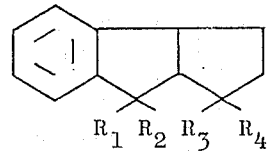

in which $R_4$ represents a group $-NR_5R_6$ in which at least one of the groups $R_5$ or $R_6$ is hydrogen to produce a compound in which said group $R_5$ or $R_6$ is converted to an alky group within the meaning given for $R_5$ alkyl $R_6$ either by direct alkylation or reductive alkylation, the above reactions if desired being carried out in combination and the product if desired being isolated as an addition salt or ester or converted from one such salt or such ester to another salt or such ester.

The following Examples illustrate the invention.

EXAMPLE 1

1,2,3,3aα,8,8aα-Hexahydro-N-methylcyclopent[a]inden-1α-amine, maleate a. 1,2,3,3aα,8,8aα-Hexahydrocyclopent[a]inden-1β-ol 3,8-Dihydrocyclopent[a]inden-1[2H]-one (1 g) in ethanol (50 ml) was stirred with Adams catalyst (50 mg) at room temperature in an atmosphere of hydrogen for 24 hours. After filtration and evaporation, the residue was dissolved in ethanol (20 ml) and a solution of sodium borohydride (0.44 g) in water (10 ml) was added and allowed to stand overnight. The solution was acidified with 2N hydrochloric acid and extracted with ether and the extracts were dried ($MgSO_4$) and evaporated to yield a yellow gum (1 g).

b. 1,2,3,3aα,8,8aα-Hexahydrocyclopent[a]inden-1β-ol, toluene-p-sulphonate ester p-Toluene sulphonyl chloride (1.3 g) was added to 1,2,3,3aα,8,8aα-hexahydrocyclopent[a]inden-1β-ol (1 g) in pyridine (10 ml) and the solution was allowed to stand for 2 days. After acidifcation with 2N hydrochloric acid the mixture was extracted with ether (4 × 25 ml) and the organic extracts were washed with saturated copper sulphate solution, dried (MgSO₄) and evaporated to yield a brown gum which crystallised on standing. This material was recrystallized from cyclohexane to yield beige crystals, m.p. 98°.

c.

1,2,3,3aα-Hexahydro-N-methylcyclopent[a]inden-1α-amine, maleate 1,2,3,3aα,8,8aα-Hexahydrocyclopent[a]inden-1β-ol, toluene-p-sulphonate ester (0.6 g) and 33% w/v methylamine in ethanol (20 ml) were heated in a bomb at 100° for 16 hours. The cooled solution was evaporated to dryness to yield an orange gum. After basification with 5N sodium hydroxide solution, the aqueous layer was extracted with ether (3 × 25 ml). The extracts were dried (MgSO₄) and filtered, and an ethereal solution of maleic acid was added. The precipitate was filtered off and recrystallised from ethanol/ether or from isopropanol to yield off-white crystals, m.p. 146°.

By a similar method the following compounds were prepared using the appropriate amine in place of methylamine:

4-(1,2,3,3aα,8,8aα-Hexahydrocyclopent[a]inden-1α-yl) morpholine, maleate, m.p. 171°.

1,2,3,3aα,8,8aα-Hexahydro-N-n-propylcyclopent[a]inden-1α-amine, maleate, m.p. 137°–8°.

N,N-Diethyl-N'(1,2,3,3aα,8,8aα-hexahydrocyclopent[a]inden-1α-yl)ethylene-diamine, dimaleate, m.p. 106.5°–107.5°.

2[(1,2,3,3aα,8,8aα-Hexahydrocyclopent[a]inden-1α-yl) amino]ethanol, m.p. 65.5°–67°.

N'-(1,2,3,3aα,8,8aα-Hexahydrocyclopent[a]inden-1α-yl)-N,N-dimethyl-1,3-propane diamine, maleate, m.p. 172°–173°.

EXAMPLE 2

N-Ethyl-1,2,3,3aα,8,8aα-hexahydrocyclopent[a]inden-1α-amine, maleate 1,2,3,3aα,8,8aα-Hexahydrocyclopent[a]inden-1β-ol toluene-p-sulphonate ester (1.0 g) and 33% w/v ethylamine in ethanol (30 ml) were heated at 80° in a bomb for 16 hours. The solvent was evaporated and the residue was basified with 2N sodium hydroxide solution and extracted with ether (3 × 30 ml). The ethereal solution was extracted with 2N hydrochloric acid (3 × 30 ml) and the latter basified and re-extracted with ether (3 × 50 ml). These last extracts were dried (MgSO₄) and evaporated and the residual oil was converted into the maleate salt. Crystallization from ethanol/ether gave fawn plates, m.p. 131°.

EXAMPLE 3

1,2,3,3aα,8,8aα-Hexahydro-N-methylcyclopent[a]inden-1β-amine, maleate

A solution of 3,8-dihydrocyclopent[a]inden-1[2H]-one (3 g) in ethanol (150 ml) and 33% w/v methylamine in ethanol (40 ml) was stirred with 10% palladium oxide on charcoal (0.3 g) in an atmosphere of hydrogen and at room temperature for 48 hours. After removal of the catalyst and evaporation of the solvent, the residue was dissolved in benzene and extracted with 2N hydrochloric acid (2 × 50 ml). The aqueous layer was made basic with 5N sodium hydroxide solution and extracted with benzene (3 × 50 ml). The benzene extract was dried (MgSO₄) and evaporated to yield a dark-red gum. This was eluted from a column of neutral alumina (150 g; Woehlm) with cyclohexane-ethyl acetate (1:1) to afford a pale yellow gum which formed a colourless maleate salt, m.p. 129°.

By a similar method the following compounds were prepared from the above ketone and corresponding amines.

1-(1,2,3,3aα,8,8aα-Hexahydrocyclopent[a]inden-1β-yl) piperidine, di-p-toluate, D-tartaric acid, m.p. 135°.

1,2,3,3aα,8,8aα-Hexahydro-N-methyl-N-phenethyl-cyclopent[a]inden-1β-amine, di-p-toluate, D-tartaric acid, m.p. 103°.

N,N-Diethyl-1,2,3,3aα,8,8aα-hexahydrocyclopent[a]inden-1β-amine, maleate, m.p. 145°.

1,2,3,3aα,8,8aα-Hexahydro-N,N-dimethyl-cyclopent[a]inden-1β-amine, D-tartaric acid, di-p-toluate, m.p. 142°.

N-Ethyl-1,2,3,3aα,8,8aα-hexahydrocyclopent[a]inden-1β-amine, maleate, m.p. 102°–4°.

EXAMPLE 4

1,2,3,3aα,8,8aα-Hexahydro-1-cyclopent[a]inden-1β-amine, maleate a. 3,3a,8,8a-Tetrahydro-cyclopent[a]inden-1[2H]-one 3,8-Dihydrocyclopent[a]inden-1[2H]-one (7.6 g.) in ethanol (400 ml) was hydrogenated at atmospheric pressure and room temperature in the presence of 10% palladium on charcoal (0.9 g) until one molar equivalent of hydrogen had been absorbed. The catalyst was filtered off and the filtrate evaporated to dryness to give a brown gum which was distilled at 90°/0.1 torr to produce a colourless oil.

b. 3,3a,8,8a-Tetrahydrocyclopent[a]inden-1[2H]-one, oxime

Sodium acetate (1 g) in water (5 ml) was added to crude 3,3a,8,8a-tetrahydrocyclopent[a]inden-1[2H]-one (0.9 g) and hydroxylamine hydrochloride (0.52 g) in ethanol (25 ml) and the mixture was heated under reflux overnight. The solvent was removed and the solid was dissolved in chloroform and washed with water (3 × 25 ml). The organic layer was dried (MgSO₄) and evaporated to yield an orange solid. Crystallization from ethanol afforded ochre crystals, m.p. 128°.

c.

1,2,3,3aα,8,8aα-Hexahydro-1-cyclopent[a]inden-1β-amine, maleate

The oxime (0.7 g) in ethanol (30 ml) containing conc. hydrochloric acid (1 ml) was hydrogenated in the presence of 10% palladium on charcoal (0.2 g) at atmospheric pressure and room temperature until uptake of hydrogen ceased. The catalyst was filtered off and the filtrate was evaporated to dryness. The residue was dissolved in 2N hydrochloric acid (25 ml) and extracted with ether (3 × 25 ml). The aqueous phase was basified with ice-cold 2N sodium hydroxide solution and again extracted with ether (3 × 25 ml). The latter extracts were dried (MgSO₄) and evaporated to give a clear gum. This was converted into a maleate salt to afford white needles, m.p. 125°. (ether - ethylacetate).

EXAMPLE 5

1,2,3,3aα,8,8aα-Hexahydro-1-cyclopent[a]inden-1β-amine, maleate

A solution of 3,8-dihydrocyclopent[a]inden-1[2H]-one oxime (1 g) in ethanol (100 ml) and conc. hydrochloric acid (1 ml) was hydrogenated over 10 % palladium oxide on charcoal (0.2 g) for 24 hours. After filtration and evaporation of the filtrate a white solid remained. This was taken up into water (50 ml), basified with 2N sodium hydroxide solution and extracted with ether (3 × 25 ml). The ether extracts were dried ($Na_2SO_4$) and evaporated to yield a gum. This was converted into the maleate in ethanol/ether and one recrystallisation from the same solvent system afforded white needles, m.p. 125°.

EXAMPLE 6

1,2,3,3aα,8,8aα-Hexahydrocyclopent[a]inden-1β-yl urea 1,2,3,3aα,8,8aα-Hexahydrocyclopent[a]inden-1β-amine (1.0 g), ethanol (2 ml), sodium cyanate (1.5 g) and water (125 ml) were heated to 60°–80° for 1 hour, chilled overnight. The colourless solid was filtered off and recrystallized from aqueous ethanol to give white crystals, m.p. 191°–192.5°.

EXAMPLE 7

1,2,3,3aα,8,8aα-Hexahydro-8,8-dimethyl-cyclopent[a]inden-1β-amine, di-p-toluoyl tartarate a.

3,8-Dihydro-8,8-dimethylcyclopent[a]inden-1[2H]-one

Sodium hydride (50% dispersed in oil) (6 g) was added to an ice cold solution of 3,8-dihydrocyclopent[a]inden-1[2H]-one (10 g) in dry dimethylformamide (100 ml). After 10 minutes methyl iodide (15 ml) was added with stirring. After 1 hour the mixture was added to water (500 ml) and extracted with ether (3 × 50 ml). The extracts were washed with water (50 ml), dried ($MgSO_4$) and evaporated to yield a brown semi-solid which crystallized from cyclohexane to give light brown crystals, m.p. 114°.

b.

3,8-Dihydro-8,8-dimethylcyclopent[a]inden-1[2H]-one, oxime

Sodium acetate (6.3 g) in water (30 ml) was added to a solution of 3,8-dihydro-8,8-dimethylcyclopent[a]inden-1[2H]-one (5.8 g) and hydroxylamine hydrochloride (3.3 g) in ethanol (60 ml) and the mixture was heated under reflux overnight. The cooled solution deposited crystals which were filtered off, washed with water and dried, m.p. 208°.

c.

1,2,3,3aα,8,8aα-Hexahydro-8,8-dimethyl-cyclopent[a]inden-1β-amine, di-p-toluoyl-d-tartrate Nickel-aluminum alloy (1.0 g) was added to a stirred solution of 3,8-dihydro-8,8-dimethylcyclopent[a]inden-1[2H]-one oxime (1.0 g) in ethanol (25 ml) and 2N sodium hydroxide solution (25 ml) at room temperature. After 1 hour a second portion of alloy (1.0 g) was added and after being stirred for a further hour the suspension was filtered. The filtrate was extracted with chloroform (3 × 20 ml). The extracts were dried ($MgSO_4$) and evaporated to give a yellow oil. This was dissolved in ether and converted into the di-p-toluoyl-d-tartrate salt, m.p. 178.5°–179.5°.

Similarly was prepared using 1,4 dibromobutane. 1,2,3,3aα,8,8aα-Hexahydrospiro(cyclopentane-8-cyclopent[a]inden)-1β-amine, di-p-toluoyl-d-tartrate salt, m.p. 172°–4°.

EXAMPLE 8

8,8-Dibenzyl-1,2,3,3aα,8,8aα-hexahydro-N-methylcyclopent[a]inden-1-amine, maleate a.

8,8-Dibenzyl-3,8-dihydrocyclopent[a]inden-1[2H]-one

A solution of the ketone (1 g) in dimethoxyethane (15 ml) was added dropwise to a stirred suspension of sodium hydride (250 mg) in dimethoxyethane (15 ml). After the sodium salt had formed, a solution of benzyl bromide (2.5 g) in dimethoxyethane (20 ml) was added dropwise over 10 minutes. Stirring was continued overnight. The excess of hydride was decomposed by the dropwise addition of water and the mixture evaporated to dryness. The residue was extracted with ethyl acetate (3 × 25 ml) and the solution dried ($MgSO_4$) and evaporated to leave a dark green solid (1.3 g). This was boiled with light petroleum (b.p. 80°–100°) and charcoal and the mixture filtered. Cooling afforded colourless granules, m.p. 155°.

b.

8,8-Dibenzyl-1,2,3,3aα,8,8aα-Hexahydro-N-methylcyclopent[a]inden-1β-amine

A solution of 8,8-dibenzyl-3,8-dihydrocyclopent[a]inden-1[2H]-one (3 g) in ethanol (100 ml) was hydrogenated over 10% palladium oxide on charcoal catalyst (1 g). After uptake of hydrogen had ceased, catalyst and solvent were removed to leave a colourless gum (3 g). A solution of the gum (1 g) in 33% ethanolic methylamine (20 mls) was hydrogenated over 5% platinum on charcoal catalyst (500 mg). After uptake of hydrogen had ceased catalyst and solvent were removed to leave a colourless gum (1 g) which afforded a maleate salt from ether as colourless microcrystals m.p. 188°.

EXAMPLE 9

1,2,3,3aα,8,8aα-Hexahydro-N,1-dimethyl-N-isopropyl-cyclopent[a]inden-1β-amine, hydrochloride, monohydrate a.

3,3a,8,8a-Tetrahydro-N-isopropylcyclopent[a]iden-1[2H]-imine 3,3a,8,8a-Tetrahydrocyclopent[a]inden-1[2H]-one (1.7 g), isopropylamine (1 g) and concentrated hydrochloric acid (1 drop) were kept at room temperature for 2 days and then dried over potassium hydroxide pellets for 2 days. Distillation in vacuo gave a colourless oil, b.p. 100°/0.1 torr.

b.

(3,3a,8,8a-Tetrahydrocyclopent[a]inden-1[2H]-ylidene) isopropyl methyl ammonium iodide 3,3a,8,8a-Tetrahydro-N-isopropylcyclopent[a]inden-1[2H]-imine (1.4 g) and methyl iodide (3 ml) were kept at room temperature overnight. The resultant solid mass was triturated with ether to give the quaternary salt as a buff solid, m.p. 168°–170°.

c.
1,2,3,3aα,8,8aα-Hexahydro-N,1-dimethyl-N-isopropyl-cyclopent[a]inden-1β-amine, hydrochloride, monohydrate (3,3a,8,8a-Tetrahydrocyclopent[a]inden-1[2H]-ylidene)isopropyl methylammonium iodide (1 g) was added portionwise to a stirred 2.18 M solution of methyl lithium in ether (20 ml), under nitrogen. After 2 days the excess of lithium reagent was decomposed with water and the ether layer was separated, dried, and evaporated. The residue was chromatographed on alumina (20 g; Laporte 'H') with cyclohexane to give a colourless gum which was converted into its hydrochloride salt. Recrystallization from ethyl acetate gave white microcrystals, m.p. 215°.

EXAMPLE 10

1,2,3,3aα,8,8aα-Hexahydro-N,N-dimethylcyclopent[a]inden-1α-amine, maleate 1,2,3,3aα,8,8aα-Hexahydrocyclopent[a]inden-1α-amine (0.4 g), formic acid (100%) (6 ml) and aqueous formaldehyde (36%) (4.2 ml) were heated at 100° overnight. The cooled solution was basified with 5N sodium hydroxide and extracted with ether (3 × 20 ml). The dried ($Na_2SO_4$) extracts were evaporated to give a yellow gum. This was converted into the maleate salt. Recrystallization from ethyl acetate/ether afforded off-white microcrystals m.p. 140°.

EXAMPLE 11

4'-Fluoro-[(1,2,3,3aα,8,8aα-hexahydrocyclopent[a]inden-1α-yl) methylamine]butyrophenone, hydrochloride 1,2,3,3aα,8,8aα-Hexahydro-N-methylcyclopent[a]inden-1α-amine, maleate (3 g), 4-chloro-4'-fluorobutyrophenone (2 g), potassium carbonate (6.0 g), sodium iodide (300 mg) and 2-butanone (30 ml) were stirred and heated under reflux for 5 days. The mixture was allowed to cool, the solid filtered off and the filtrate evaporated. The residue was dissolved in ethyl acetate, treated with ethereal hydrogen chloride, and the precipitate filtered off and discarded. The filtrate was extracted with 2N hydrochloric acid (5 × 25 ml) and the combined extracts were basified with 2N sodium hydroxide solution and extracted with ethyl acetate (2 × 25 ml). Evaporation of the dried extracts left a gum (1 g) which was eluted from an alumina column (30 g; Laporte 'H') with cyclohexane:ethyl acetate (2:1) to give the title compound as a gum (400 mg). A solution of this in warm ethyl acetate was treated with ethereal hydrogen chloride. Cooling afforded colourless microcrystals, m.p. 199°.

EXAMPLE 12

1,2,3,3aα,8,8aα-Hexahydro-N-isopropyl-N-methylcyclopent[a]inden-1α-amine 1,2,3,3aα,8,8aα-Hexahydro-N-methylcyclopent[a]inden-1α-amine (2.22 g) was dissolved in ethanol (25 ml), acetone (10 ml) added and the mixture allowed to stand for 30 minutes. The solution was then hydrogenated over 5% palladium on charcoal (2.0 g) until one mole of hydrogen had been absorbed. Filtration of catalyst, followed by evaporation of solvent, afforded a colourless oil (2.6 g) which was converted into a di-p-toluoyl tartrate. Recrystallization from methanol/ethyl acetate yielded colourless microcrystals, m.p. 168°–168.5°.

EXAMPLE 13

Pharmaceutical compositions (The active ingredient in these compositions is AH 9197 referred to in Table I; this may be replaced by another active compound according to the invention, if desired)

TABLETS

To prepare 10,000 tablets each containing the equivalent of 30 mg AH 9197.

Mix together 485 g AH 9197 maleate (equivalent to 300 g AH 9197) with 765 g of calcium sulphate dihydrate and sufficient of a 5% solution of low viscosity sodium carboxymethylcellulose to produce a damp cohesive mass. Granulate the damp mass by passing through a 16 mesh sieve and mix the sieved granules with 240 g of maize starch and 10 g of magnesium stearate.

Compress the lubricated granules on a suitable tablet machine using 8 mm diameter normal concave punches to produce tablets each weighing 150 mg.

If desired the tablets may be film coated.

If compressed on 8 mm deep concave punches the tablets may be sugar coated by conventional means.

SUPPOSITORIES

To prepare 1,000 suppositories each containing the equivalent of 50 mg AH 9197.

Disperse 81 g of finely powdered AH 9197 maleate (equivalent to 50 g of AH 9197) in sufficient molten Witepsol H15 suppository base so that each 2 g of the mixture contains 81 mg of AH 9197 maleate.

Pour the molten mixture into suitable plastic moulds ensuring the powder remains evenly dispersed and cool.

AMPOULES

To prepare 1,000 × 5 ampoules containing 5 mg/ml of AH 9197.

Disperse 25 g of AH 9197 in freshly collected Water for Injections and add hydrochloric acid BP until all the powder has dissolved. Dissolve 40 g sodium chloride in the resultant solution. Pass the solution through a 1.2 M membrane filter and pack in 5 ml ampoules. Sterilize by heating in an autoclave.

CAPSULES

To prepare 5,000 capsules each containing the equivalent of 60 mg AH 9197.

Mix together 485 g of powdered AH 9197 maleate (equivalent to 300 g AH 9197) with 5.5 g microcrystalline cellulose BPC. Subdivide by means of a suitable filling machine into No. 3 hard gelatin capsules so that each capsule contains 100 mg of the mixtures.

I claim:

1. Compounds of the general formula:

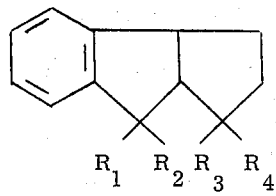

in which:

R₁ and R₂ represent a hydrogen atom, a $C_{1-6}$ alkyl group, or a benzyl group, or together form a cycloalkyl ring containing from 3 to 6 carbon atoms;

R₃ represents a hydrogen atom or a $C_{1-6}$ alkyl group;

R₄ represents the group NR₅R₆ in which R₅ and R₆ may be the same or different, each represent a hydrogen atom, or a $C_{1-6}$ alkyl radical, which $C_{1-6}$ alkyl radical may optionally be substituted by an amino, $C_{1-6}$ alkylamino, $C_{1-6}$ dialkylamino, hydroxy, phenyl or benzoyl groups which benzoyl groups may be further substituted by halogen; and nontoxic pharmaceutically acceptable salts.

2. Compounds as claimed in claim 1 in which R₁, or R₁ and R₂ represent alkyl groups containing from 1 to 4 carbon atoms.

3. Compounds as claimed in claim 1, in which the alkyl groups contain from 1 to 4 carbon atoms.

4. Compounds as claimed in claim 1 in which R₅, or R₅ and R₆ represent alkyl groups containing from 1 to 6 carbon atoms.

5. Compounds as claimed in claim 4 in which the alkyl groups contain from 1 to 4 carbon atoms.

6. Compounds as claimed in claim 1 in the form of acid addition salts with mineral or organic acids.

7. Salts as claimed in claim 6 in which the acid is hydrochloric, maleic or tartaric.

8. Compounds as claimed in claim 1 in which R₁, R₂ or R₁ and R₂ represents hydrogen, $C_{1-4}$ alkyl, or benzyl, or together form a cyclopentyl ring, R₃ represents hydrogen or $C_{1-4}$ alkyl and R₅, R₆ or R₅ and R₆ represents hydrogen, $C_{1-4}$ alkyl which may optionally be substituted bu $C_{1-4}$ alkylamino or by $C_{1-4}$ dialkylamino or by phenyl or by 4-fluorobenzoyl.

9. The compound of claim 1 which is 1,2,3,3aα,8,8aα-Hexahydro-N-methylcyclopent[a]inden-1α-amine, maleate.

10. The compound of claim 1 which is 1,2,3,3aα,8,8aα-Hexahydro-N-n-propylcyclopent[a]inden-1α-amine, maleate.

11. The compound of claim 1 which is N,N-Diethyl-N'(1,2,3,3aα,8,8aα-hexahydrocyclopent[a]inden-1α-yl) ethylene-diamine, dimaleate.

12. The compound of claim 1 which is 2[(1,2,3,3aα-8,8aα-hexahydrocyclopent[a]inden-1α-yl)amino]ethanol.

13. The compound of claim 1 which is N'-(1,2,3,3aα-8,8aα-Hexahydrocyclopent[a]inden-1α-yl)-N,N-dimethyl-1,3-propane diamine, maleate.

14. The compound of claim 1 which is N-Ethyl-1,2,3,3aα,8,8aα-hexahydrocyclopent[a]inden-1α-amine, maleate.

15. The compound of claim 1 which is 1,2,3,3aα,8,8aα-Hexahydro-N-methylcyclopent[a]inden-1β-amine, maleate.

16. The compound of claim 1 which is 1,2,3,3aα,8,8aα-Hexahydro-N-methyl-N-phenethylcyclopent[a]inden-1β-amine, di-p-toluate D-tartaric acid.

17. The compound of claim 1 which is N-N-Diethyl-1,2,3,3aα,8,8aα-hexahydrocyclopent[a]inden-1β-amine, maleate.

18. The compound of claim 1 which is 1,2,3,3aα,8,8aα-Hexahydro-N,N-dimethyl-cyclopent[a]inden-1β-amine, di-p-toluate D-tartaric acid.

19. The compound of claim 1 which is N-Ethyl-1,2,3,3aσ,8,8aα-hexahydrocyclopent[a]inden-1β-amine, maleate.

20. The compound of claim 1 which is 1,2,3,3aα,8,8aα-Hexahydro-1-cyclopent[a]inden-1β-amine, maleate.

21. The compound of claim 1 which is 1,2,3,3aα,8,8aα-Hexahydro-8,8-dimethyl-cyclopent[a]inden-1β-amine, di-p-toluoyl tartrate.

22. The compound of claim 1 which is 1,2,3,3aα,8,8aα-Hexahydrospiro(cyclopentane-8-cyclopent[a]inden)-1β-amine, di-p-toluoyl-D-tartrate salt.

23. The compound of claim 1 which is 8,8-Dibenzyl-1,2,3,3aα,8,8aα-hexahydro-N-methylcyclopent[a]inden-1-amine, maleate.

24. The compound of claim 1 which is 1,2,3,3aα,8,8aα-Hexahydro-N,1-dimethyl-N-isopropyl-cyclopent[a]inden-1β-amine, hydrochloride, monohydrate.

25. The compound of claim 1 which is 1,2,3,3aα,8,8aα-Hexahydro-N,N-dimethylcyclopent[a]inden-1α-amine, maleate.

26. The compound of claim 1 which is 4'-Fluoro-[(1,2,3,3aα,8,8aα-hexahydrocyclopent[a]inden-1α-yl)methyl-amino]butyrophenone, hydrochloride.

27. The compound of claim 1 which is 1,2,,3,3aα,8,8aα-Hexahydro-N-isopropyl-N-methylcyclopent[a]inden-1α-amine.

\* \* \* \* \*